US00PP37322P2

(12) United States Plant Patent
van Dijk

(10) Patent No.: US PP37,322 P2
(45) Date of Patent: Mar. 10, 2026

(54) ***ANTHURIUM* PLANT NAMED 'AN2244532'**

(50) Latin Name: *Anthurium andreanum*
Varietal Denomination: AN2244532

(71) Applicant: ANTHURA B.V., Bleiswijk (NL)

(72) Inventor: Jan van Dijk, Bleiswijk (NL)

(73) Assignee: ANTHURA B.V., Bleiswijk (NL)

( * ) Notice: Subject to any disclaimer, the term of this patent is extended or adjusted under 35 U.S.C. 154(b) by 0 days.

(21) Appl. No.: 19/315,583

(22) Filed: Aug. 31, 2025

(51) Int. Cl.
*A01H 5/02* (2018.01)
*A01H 6/10* (2018.01)

(52) U.S. Cl.
USPC ..... Plt./365
CPC ..... *A01H 6/10* (2018.05)

(58) Field of Classification Search
USPC ..... Plt./365
CPC ..... A01H 5/02
See application file for complete search history.

*Primary Examiner* — Kent L Bell
(74) *Attorney, Agent, or Firm* — C. Anne Whealy

(57) ABSTRACT

A new and distinct cultivar of *Anthurium* plant named 'AN2244532', characterized by its upright to outwardly arching plant habit; freely clumping growth habit; bushy and dense plants; ovate to lanceolate-shaped dark green-colored leaves; freely flowering habit; open inflorescences that are positioned above the foliar plane on strong scapes; ovate-shaped dark red-colored spathes; and white to deep pink-colored spadices.

2 Drawing Sheets

Figure 1:
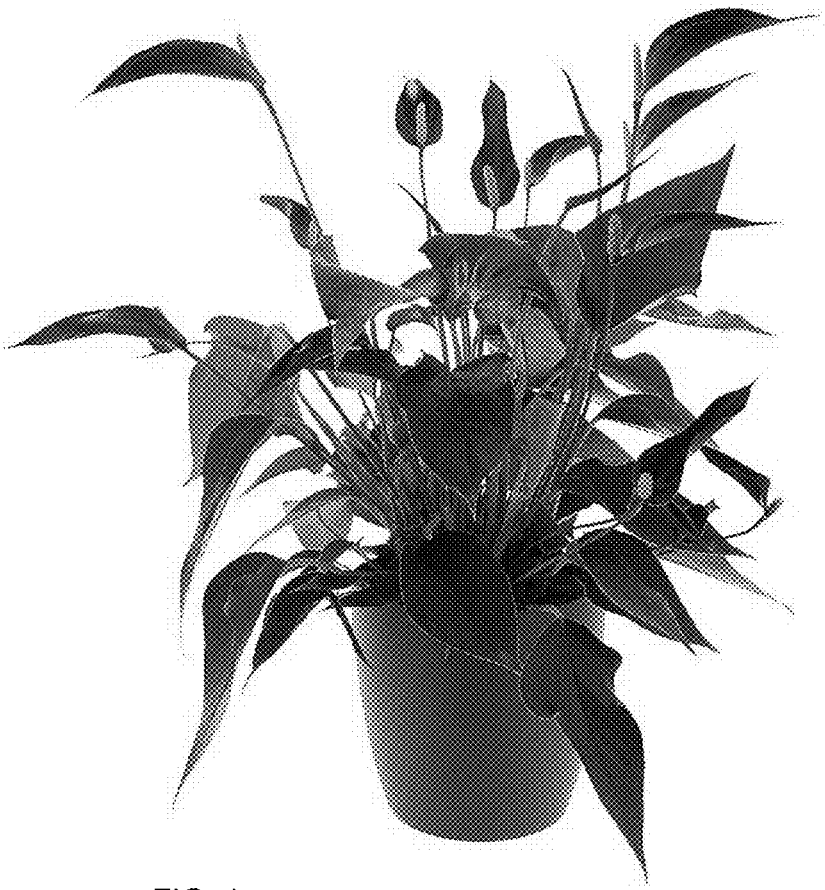

Botanical designation: *Anthurium andreanum.*
Cultivar denomination: 'AN2244532'.

CROSS-REFERENCED TO CLOSELY-RELATED APPLICATION

A European Community Plant Breeder's Rights application for the instant plant was filed by the Applicant/Assignee of the instant application, Anthura B.V. of Bleiswijk, The Netherlands on Nov. 20, 2024, application number 2024/2692. Foreign priority is not claimed to this application.

BACKGROUND OF THE INVENTION

The present invention relates to a new and distinct cultivar of *Anthurium* plant, botanically known as *Anthurium andreanum*, commonly referred to as Flamingo Flower and hereinafter referred to by the name 'AN2244532'.

The new *Anthurium* plant is a product of a controlled breeding program conducted by the Inventor in Bleiswijk, The Netherlands. The objective of the breeding program is to create new *Anthurium* plants with durable dark red-colored spathes.

The new *Anthurium* plant originated from a cross-pollination made by the Inventor in October 2015 in Bleiswijk, The Netherlands of a proprietary breeding selection of *Anthurium andreanum* identified as code number 13-031903-0002, not patented, as the female, or seed, parent with a proprietary breeding selection of *Anthurium andreanum* identified as code number 13-033728-0009, not patented, as the male, or pollen, parent. The new *Anthurium* was discovered and selected by the Inventor as a single flowering plant within the progeny of the stated cross-pollination in a controlled greenhouse environment in Bleiswijk, The Netherlands in July 2017.

Asexual reproduction of the new *Anthurium* plant by in vitro meristem propagation in a controlled environment in Bleiswijk, The Netherlands since November 2019 has shown that the unique features of this new *Anthurium* are stable and reproduced true to type in successive generations of asexual reproduction.

SUMMARY OF THE INVENTION

Plants of the new *Anthurium* have not been observed under all possible combinations of environmental conditions and cultural practices. The phenotype may vary somewhat with variations in environment conditions such as temperature and light intensity, without, however, any variance in genotype.

The following traits have been repeatedly observed and are determined to be the unique characteristics of 'AN2244532'. These characteristics in combination distinguish 'AN2244532' as a new and distinct *Anthurium* plant:

1. Upright to outwardly arching plant habit.
2. Freely clumping growth habit; bushy and dense plants.
3. Ovate to lanceolate-shaped dark green-colored leaves.
4. Freely flowering habit.
5. Open inflorescences that are positioned above the foliar plane on strong scapes.
6. Ovate-shaped dark red-colored spathes.
7. White to deep pink-colored spadices.

Plants of the new *Anthurium* differ primarily from plants of the female parent selection in the following characteristics:

1. Spathes of plants of the new *Anthurium* are darker red in color than spathes of plants of the female parent selection.
2. Developing spadices of plants of the new *Anthurium* are white in color whereas developing spadices of plants of the female parent selection are pink in color.

Plants of the new *Anthurium* differ primarily from plants of the male parent selection in the following characteristics:

1. Spadices of plants of the new *Anthurium* are shorter than spadices of plants of the male parent selection.

2. Spadices of plants of the new *Anthurium* are less tapering towards the apex than spadices of plants of the male parent selection.

Plants of the new *Anthurium* can also be compared to plants of *Anthurium andreanum* 'AN2562165', disclosed in U.S. Plant Pat. No. 34,077. In side-by-side comparisons, plants of the new *Anthurium* differ primarily from plants of 'AN2562165' in the following characteristics:

1. Spadices of plants of the new *Anthurium* are positioned higher above the foliar plane than spadices of plants of 'AN2562165'.
2. Spathes of plants of the new *Anthurium* are smaller than spathes of plants of 'AN2562165'.
3. Spadices of plants of the new *Anthurium* are less tapering towards the apex than spadices of plants of 'AN2562165'.

BRIEF DESCRIPTION OF THE PHOTOGRAPHS

The accompanying photographs illustrate the overall appearance of the new *Anthurium*. The photographs show the colors as true as it is reasonably possible to obtain in colored reproductions of this type. Colors in the photographs may differ slightly from the color values cited in the detailed botanical description which accurately describe the colors of the new *Anthurium*.

The photograph on the first sheet (FIG. 1) is a side perspective view of a typical plant of 'AN2244532' grown in a container.

Figure 2:
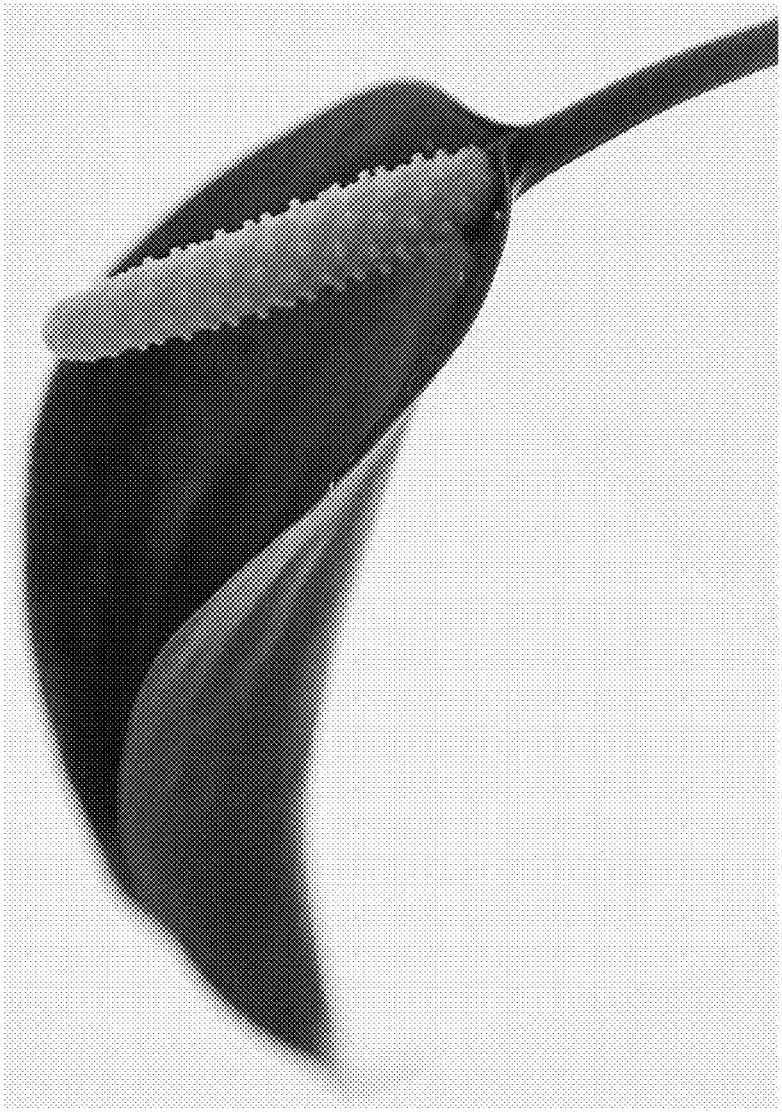

The photograph on the second sheet (FIG. 2) is a close-up view of a typical inflorescence of 'AN2244532'.

DETAILED BOTANICAL DESCRIPTION

The aforementioned photographs and following observations and measurements describe plants grown in 14-cm containers during the winter in a glass-covered greenhouse in Bleiswijk, The Netherlands. Plants were grown under conditions and practices which approximate those generally used in commercial *Anthurium* production. During the production of the plants, day and night temperatures ranged from about 19® C. to about 22.5° C. and light levels ranged from about 100 μmol to about 200 μmol. Plants were eleven months from planting young rooted plants when the photographs and the detailed description were taken. In the following description, color references are made to The Royal Horticultural Society Colour Chart, 2015 Edition, except where general terms of ordinary dictionary significance are used.

Botanical classification: *Anthurium andreanum* 'AN2244532'.

Parentage:

*Female, or seed, parent*.—Proprietary breeding selection of *Anthurium andreanum* identified as code number 13-031903-0002, not patented.

*Male, or pollen, parent*.—Proprietary breeding selection of *Anthurium andreanum* identified as code number 13-033728-0009, not patented.

Propagation:

*Type*.—By in vitro meristem propagation.

*Time to initiate roots, summer and winter*.—About two weeks at temperatures ranging from about 19° C. to about 22.5° C.

*Time to produce a rooted young plant, summer and winter*.—About six to eight weeks at temperatures ranging from about 19° C. to about 22.5° C.

*Root description*.—Medium in thickness, fibrous; typically pink in color; actual color of the roots is dependent on substrate composition, water quality, fertilizer type and formulation, substrate temperature and physiological age of roots.

*Rooting habit*.—Freely branching, medium density.

Plant description:

*Plant shape*.—Upright to outwardly arching plant habit; overall shape, spherical.

*Growth habit*.—Freely clumping habit imparting a bushy and dense appearance; in a single year of production, about 40 individual plants can be harvested per plant; moderately vigorous growth habit and moderate growth rate.

*Plant height, from soil level to top of leaf plane*.—About 25.3 cm.

*Plant height, from soil level to top of inflorescences*.—About 38.6 cm.

*Plant diameter or spread*.—About 46.9 cm.

Leaf description:

*Arrangement*.—Alternate; simple.

*Length*.—About 13.4 cm.

*Width*.—About 7.4 cm.

*Shape*.—Ovate to lanceolate.

*Apex*.—Apiculate with a mucronate tip.

*Base*.—Obtuse.

*Margin*.—Entire; coarsely undulate.

*Texture, upper and lower surfaces*.—Smooth, glabrous; moderately coriaceous.

*Venation pattern*.—Pinnate.

*Color*.—Developing leaves, upper surface: Close to 146A. Developing leaves, lower surface: Close to 146B. Fully expanded leaves, upper surface: Close to 147A; mucronate tip, close to 9C; narrow marginal edges, close to N144A; venation, close to 144A. Fully expanded leaves, lower surface: Close to 146B; venation, close to 144B.

*Petioles*.—Length: About 14.8 cm. Diameter: Distally, about 3 mm and proximally, about 4 mm. Texture, upper and lower surfaces: Smooth, glabrous. Color, upper surface: Close to 146B. Color, lower surface: Close to a blend of 146B and 146C. Geniculum length: About 3.3 mm. Geniculum diameter: About 3 mm. Geniculum texture, upper and lower surfaces: Smooth, glabrous. Geniculum color, upper surface: Close to a blend of 146B and 146C. Geniculum color, lower surface: Close to 144B. Wing length: About 1.6 cm. Wing diameter: About 3.5 mm. Wing texture: Smooth, glabrous. Wing color: Close to N144D.

Inflorescence description:

*Inflorescence arrangement and flowering habit*.—Spathes with spadices; open inflorescences held above the foliar plane on strong scapes; flowering structures arise from leaf axils; freely and continuous flowering year-round in controlled temperature greenhouses in The Netherlands; typically about 22 developing and developed inflorescences per plant at one time; inflorescence development commences about 2.5 to 3.5 months after planting rooted young plants.

*Inflorescence longevity*.—On the plant, depending on temperature, spathes maintain good substance for about two months; inflorescences persistent.

*Fragrance*.—None detected.

*Spathes*.—Length: About 10.4 cm. Width: About 4.2 cm. Shape: Ovate; slightly concave to concave. Apex: Mucronulate. Base: Rounded. Margin: Entire; involute. Aspect: About 45° to 55° from the scape axis. Texture, upper and lower surfaces: Smooth, glabrous; moderately coriaceous. Color: When developing, front surface: Close to N45A; proximal half, close to a blend of 46A and 187B; mucronulate apex, close to 187B and at the tip, close to 8C. When developing, rear surface: Close to 46A; proximal half, close to 183A; mucronulate apex, close to 187A and at the tip, close to 8C. Fully developed, front surface: Close to a blend of 187B and 187C; towards the margins, close to 187A; mucronulate apex, close to 187B and at the tip, close to 151B; with subsequent development, color becoming closer to 200B. Fully developed, rear surface: Close to 185A; towards the margins, close to 187B; mucronulate apex, close to 187B and at the tip, close to 151B; with subsequent development, color becoming closer to 146C.

*Spadices*.—Length: About 2.7 cm. Diameter: About 6 mm. Shape: Cylindrical, slightly tapering towards the apex; apex, obtuse; base, obtuse; in cross-section, rounded. Aspect: About 10° to 25° from the scape axis. Color: Immature: Close to NN155A; towards the apex, close to 144A to 144B. Mature: Close to 51B. Flowers: Type: Hermaphroditic. Quantity per spadix: About 120. Height: Less than 1 mm. Diameter: About 2 mm. Shape: Roughly square. Anther color: Close to 155D. Pollen amount: Scarce. Pollen color: Close to 155D. Stigma color: Close to 155D.

*Scapes*.—Length: About 25.5 cm. Diameter: About 2 mm. Strength: Strong, sturdy. Aspect: About 25° from vertical. Color: Close to 146B; distally, occasionally tinged with close to 183C; at the base of the spathe, close to 46B.

*Seed and fruit*.—To date, seed and fruit development has not been observed on plants of the new *Anthurium*.

Pathogen & pest resistance: To date, plants of the new *Anthurium* have not been observed to be resistant to pathogens or pests common to *Anthurium* plants.

Temperature tolerance: Plants of the new *Anthurium* have been observed to be tolerant to high temperatures of about 30° C. and to be hardy to USDA Hardiness Zone 10.

It is claimed:

1. A new and distinct *Anthurium* plant named 'AN2244532' as herein illustrated and described.

* * * * *